US009002462B2

(12) United States Patent
McClure et al.

(10) Patent No.: US 9,002,462 B2
(45) Date of Patent: Apr. 7, 2015

(54) DOWNLOADABLE FILTERS FOR A VISUAL PROSTHESIS

(71) Applicant: Second Sight Medical Products, Inc., San Fernando, CA (US)

(72) Inventors: Kelly H McClure, Simi Valley, CA (US); Arup Roy, Valencia, CA (US); Sumit Yadav, Los Angeles, CA (US); Pishoy Maksy, Newport Beach, CA (US); Peter Melistrup, Seattle, WA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 13 days.

(21) Appl. No.: 14/046,815

(22) Filed: Oct. 4, 2013

(65) Prior Publication Data

US 2014/0142660 A1 May 22, 2014

Related U.S. Application Data

(62) Division of application No. 11/923,813, filed on Oct. 25, 2007, now Pat. No. 8,571,668, and a division of application No. 11/523,257, filed on Sep. 18, 2006, now Pat. No. 8,224,454.

(60) Provisional application No. 60/718,096, filed on Sep. 16, 2005.

(51) Int. Cl.
*A61N 1/00* (2006.01)
*A61N 1/36* (2006.01)
*A61N 1/05* (2006.01)

(52) U.S. Cl.
CPC ........... *A61N 1/36046* (2013.01); *A61N 1/0543* (2013.01)

(58) Field of Classification Search
CPC .................................................. A61N 1/36046
USPC ...................................................... 607/53–54
See application file for complete search history.

(56) References Cited

U.S. PATENT DOCUMENTS

| 4,573,481 A | 3/1986 | Bullara |
| 4,628,933 A | 12/1986 | Michelson |
| 4,837,049 A | 6/1989 | Byers et al. |

(Continued)

FOREIGN PATENT DOCUMENTS

| WO | WO 02/40095 A1 | 5/2002 |
| WO | WO 02/089912 A2 | 11/2002 |
| WO | WO 03/061537 A1 | 7/2003 |

*Primary Examiner* — Nicole F Lavert
(74) *Attorney, Agent, or Firm* — Scott B. Dunbar; Alessandro Steinfl; Jean Yang-Scharlotta (57) ABSTRACT

The present invention is an improved method of providing flexible image possessing in a visual prosthesis by providing downloadable video filters. In a visual prosthesis, the input video image is normally higher resolution than the output stimulation of the retina, optic nerve or visual cortex. It is advantageous to apply video processing algorithms (filters) to help provide the most useful information to the lower resolution electrode array. Different filters are more effective in different environments and for different subjects. Examples of situation dependent filters include reverse image, contrast increasing, edge detection, segmentation using chromatic information and motion detection. Filters loaded in the video processing unit may be selected dynamically to suit the situation or the user's preference. It is therefore advantageous to provide flexibility in applying filters. However, it is also important to maintain the security necessary for a medical device.

15 Claims, 5 Drawing Sheets

(56) References Cited

U.S. PATENT DOCUMENTS

| | | |
|---|---|---|
| 5,109,844 A | 5/1992 | de Juan, Jr. et al. |
| 5,215,088 A | 6/1993 | Normann et al. |
| 5,935,155 A | 8/1999 | Humayun et al. |
| 6,400,989 B1 | 6/2002 | Eckmiller |
| 6,458,157 B1 | 10/2002 | Suaning |
| 7,266,413 B2 | 9/2007 | Greenberg |
| 2002/0193845 A1 | 12/2002 | Greenberg |
| 2004/0172098 A1 | 9/2004 | Greenberg |

DOWNLOADABLE FILTERS FOR A VISUAL PROSTHESIS

CROSS REFERENCE TO RELATED APPLICATIONS

This application is a divisional application of, and claims priority to U.S. application Ser. No. 11/923,813, filed Oct. 25, 2007, for Downloadable Image Processing Filters for Visual Prosthesis, which is a divisional application of Ser. No. 11/523,257, filed Sep. 18, 2006, for Downloadable Filters for a Visual Prosthesis, which claims the benefit of U.S. Provisional Application No. 60/718,096, PC Downloadable Image Processing Filter for Retinal Prosthesis, filed Sep. 16, 2005, the disclosure of which is incorporated herein by reference. This application is related to U.S. patent application Ser. No. 11/413,771, filed Apr. 28, 2006, for Method and Apparatus to Provide Safety Checks for Neural Stimulation, which is incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved method of providing flexible video possessing in a visual prosthesis by providing downloadable video filters.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across retinal neuronal cell membranes, which can initiate retinal neuronal action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the retinal neurons, and avoid undue compression of the retinal neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated a cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

It is known that neurons respond best to change in stimuli. The retina, if continuously stimulated in a consistent manner, will slowly become less and less sensitive to the stimulus. This causes the perception of a constant visual image to gradually disappear. Those with normal vision are unable to perceive this effect because the eye constantly moves, motions called jitter or microsaccades. A normal retina has a resolution of approximately four million light transducer cells (rods and cones), hence it requires a minute movement to change the light intensity cast upon a given light transducer.

A retinal prosthesis, according to the present invention, has two disadvantages. First, the resolution of an electrode array applied to the retina is significantly lower than the resolution of a healthy retina, requiring a greater movement to move an image from one electrode to the next electrode, as compared to one cone to the next cone. Further, a head mounted camera does not have the natural jitter or microsaccades of an eye. Therefore it is necessary to achieve the required change in another manner.

It is also known that some neural processing is done within the retina. Hence, a continuously stimulated cone will not result in a continuous signal to the brain. Ganglion and bipolar cells pass along this change in information more readily than constant information. In a diseased retina, rods and cone cannot be stimulated, since they are dead. Electrically stimulating cells further along the neural pathway, bypasses some of the neural processing. This processing must be simulated electronically to gain normal brain stimulation.

The ability to perceive a constant image or image contrast is necessary to the design of a visual prosthesis.

SUMMARY OF THE INVENTION

The present invention is a method of neural stimulation and more specifically an improved method of providing flexible video/image possessing in a visual prosthesis by providing downloadable video filters.

In a visual prosthesis, the input video image will, for the foreseeable future, be higher resolution than the output stimulation of the retina, optic nerve or visual cortex. This is due to limitations of electrode array technology and the rapid advancement of video camera technology. It is therefore, advantageous to apply video/image processing algorithms (filters) to help provide the most useful information to the lower resolution electrode array. Different filters are more effective in different environments and for different subjects. Furthermore, these filters will continue to improve over time.

Examples of situation or environment dependent filters include reverse image, contrast increasing, edge detection, segmentation using chromatic information, and motion detection. Many other filters will be useful in providing the best possible image to a subject. Filters loaded in the video processing unit may be selected dynamically to suit the situation or the subject's preference.

It is therefore advantageous to provide flexibility in applying filters. However, it is also important to maintain the security and integrity necessary for a medical device. The present invention provides for an external (not implanted) video processing unit with downloadable video filters.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
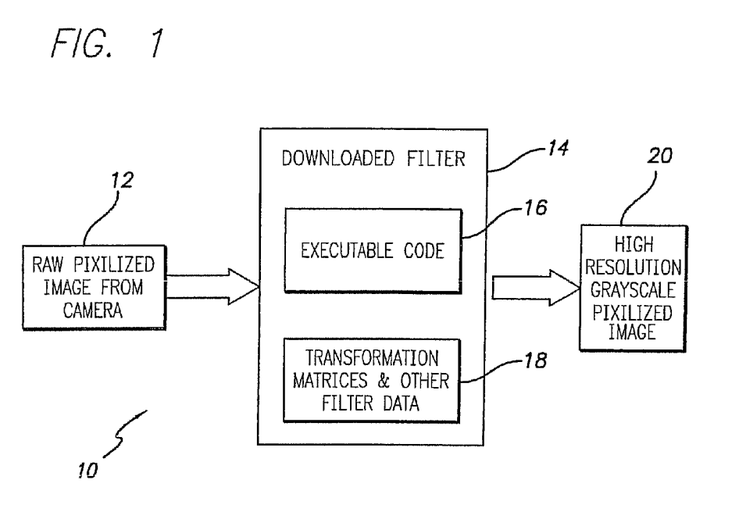
FIG. 1 depicts a block diagram of the hardware supporting downloadable filters.

Referring to FIG. 1, images from a video camera (not shown) are transferred to an input buffer 12. The image is applied to the filter 14 which includes code 16 and data 18 to generate an image in an output buffer 20. All of this takes place in a digital signal process (DSP) 10. While the preferred embodiment includes a DSP, it would be clear to one of skill in the art that the functions described here could be accomplished by a microprocessor or even separate components.

Figure 2:
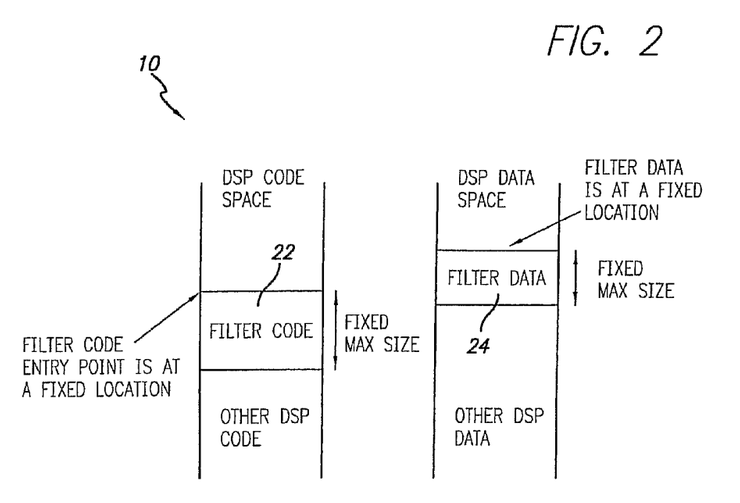
FIG. 2 depicts of block diagram of the filter download code space.

Referring to FIG. 2, the DSP 10 includes memory space for both the executable code (algorithm) and data (parameters such as transformation matrices). The down loadable filters have fixed spaces for code 22 and data 24. Note that the down loaded algorithms and parameters are assigned to, and limited to, specific memory locations. As a medical device, a visual prosthesis must have security and safety checks which prevent over stimulation of the neural tissue. Dedicated memory space, authenticity checks, and error checks, provide for the safety of the patient. However, the system must be designed such that no filter, no matter how mis-designed, can bypass important safety checks and endanger the heath of the patient. These safety checks are described in U.S. patent application Ser. No. 11/413,771, filed Apr. 28, 2006 for Method and Apparatus to Provide Safety Checks for Neural Stimulation, which is incorporated herein by reference.

Figure 3:
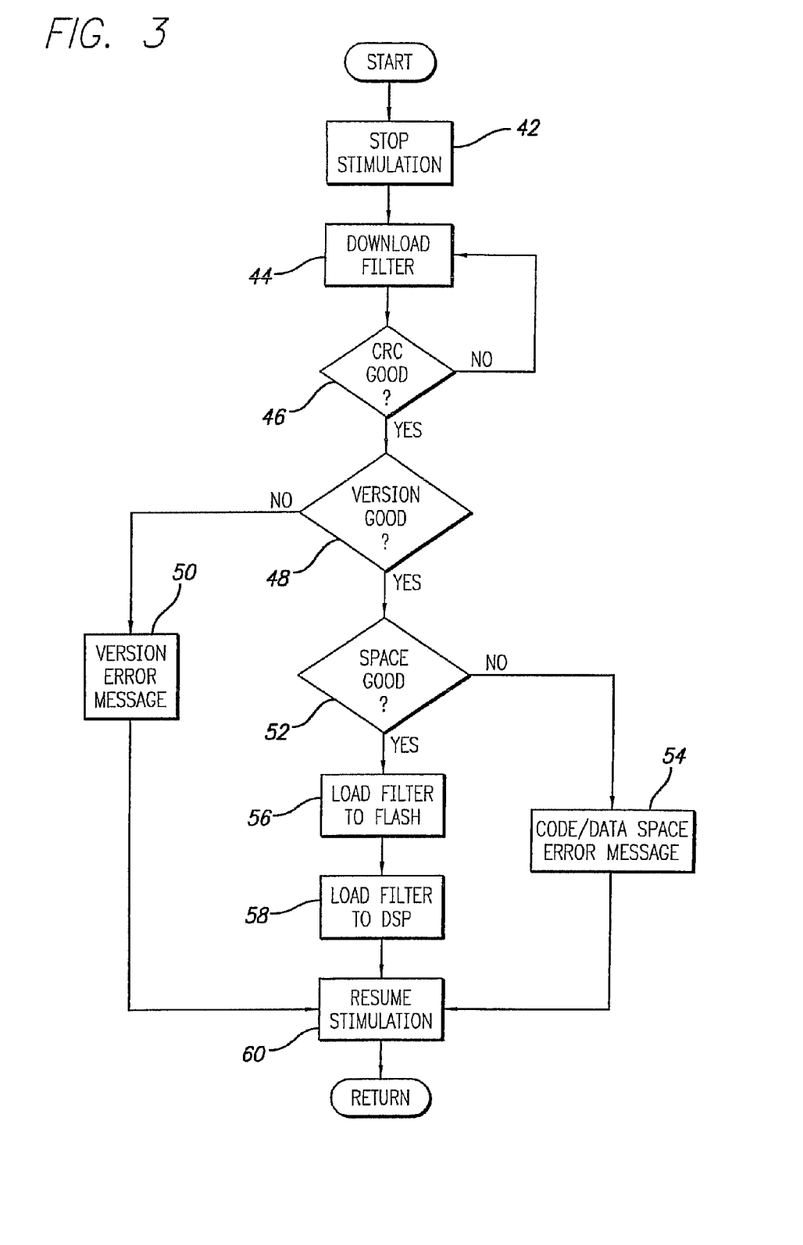
FIG. 3 is a flow chart showing the filter download process.
Figure 4:
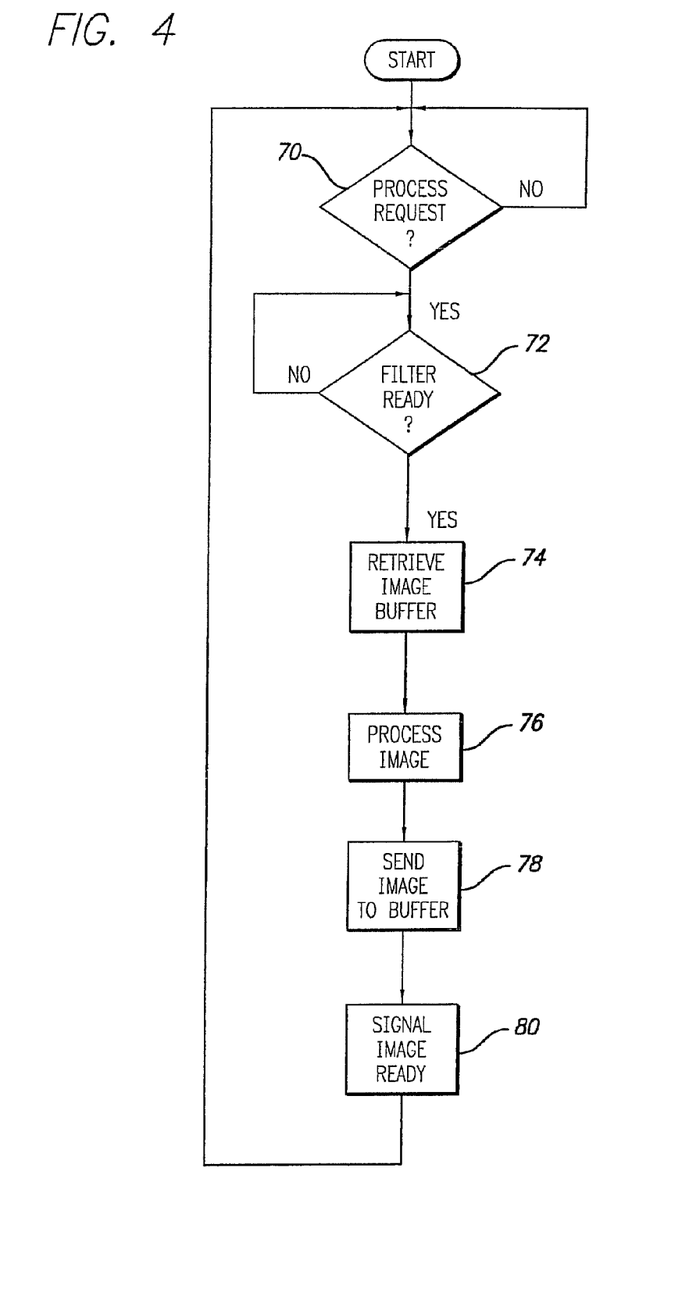
FIG. 4 is a flowchart of the stimulation process using downloadable filters.

Referring to FIG. 3, the download process begins by interrupting the stimulation process 42 as shown in FIG. 4. This is necessary for safety to insure that no stimulation is attempted with a partially loaded filter. Next the filter is downloaded from a linked computer (not shown) 44. Many peer to peer communication protocols are well known and can be used for this purpose. The preferred embodiment uses a Universal Serial Bus (USB) interface. Next, a cyclic redundancy check (CRC) is preformed 46 to ensure data integrity. If there are any errors, the filter download is restarted or retried.

Next, the system performs a version control check 48. Each filter includes a table of compatible firmware versions. If the filter is incompatible with the firmware version an error message is returned to the linked computer 50 and the download process is terminated. If the version is compatible, a space check is performed 52. The DSP has finite fixed space for code and data. If either is too large, an error message is returned to the linked computer 54 and the download process is terminated. If there is adequate space for code and data, the filter is downloaded and written to non-volatile memory 56. In the preferred embodiment non-volatile memory is flash memory. The filter is then written to DSP memory 58 and stimulation is restarted 59. Since the internal memory in the DSP is volatile, the flash memory provides backup when power is lost.

FIG. 4, shows the stimulation process. When a new frame is ready, the master process sends a process request to the filter process. The filter process continuously checks for a new process request 70. This is done by a time slice method in the DSP. Hence, the filter is not tying up the processor looking for process requests. If there is a process request, the filter process checks to see if the filter is ready 72. The filter may not be ready if it is in the process of a download as described with respect to FIG. 3. If ready, the system retrieves the image from an input buffer 74, processes the image according to the filter 76, and sends the resulting image to the output buffer 78. Finally, it sends a signal that the image is ready in the output buffer and returns to wait for a new process request.

Figure 5:
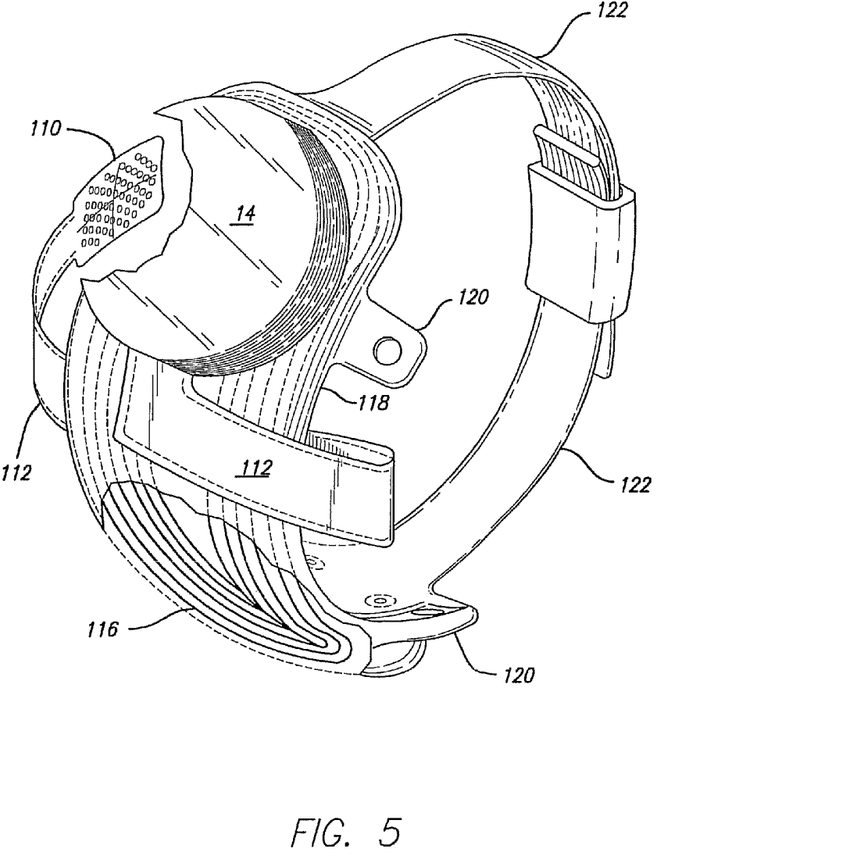
FIG. 5 is a perspective view of the implanted portion of the preferred visual prosthesis.

FIG. 5 shows a perspective view of the implanted portion of the preferred retinal prosthesis. An electrode array 110 is mounted by a retinal tack or similar means to the epiretinal surface. The electrode array 110 is electrically coupled by a cable 112, which pierces the sclera and is electrically coupled to an electronics package 114, external to the sclera.

The electronics package 114 is electrically coupled to a secondary inductive coil 116. Preferably the secondary inductive coil 116 is made from wound wire. Alternatively, the secondary inductive coil may be made from a thin film polymer sandwich with wire traces deposited between layers of thin film polymer. The electronics package 114 and secondary inductive coil 116 are held together by a molded body 118. The molded body 18 may also include suture tabs 120. The molded body narrows to form a strap 122 which surrounds the sclera and holds the molded body 118, secondary inductive coil 116, and electronics package 114 in place. The molded body 118, suture tabs 120 and strap 122 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 116 and molded body 118 are preferably oval shaped. A strap can better support an oval shaped coil.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. It is an advantage of the present design, that the entire implanted portion of the prosthesis is attached to and supported by the sclera. By placing the device under the rectus muscles with the electronics package in an area of fatty issue between the rectus muscles, eye motion does not cause any flexing which might fatigue, and eventually damage, the device.

Figure 6:
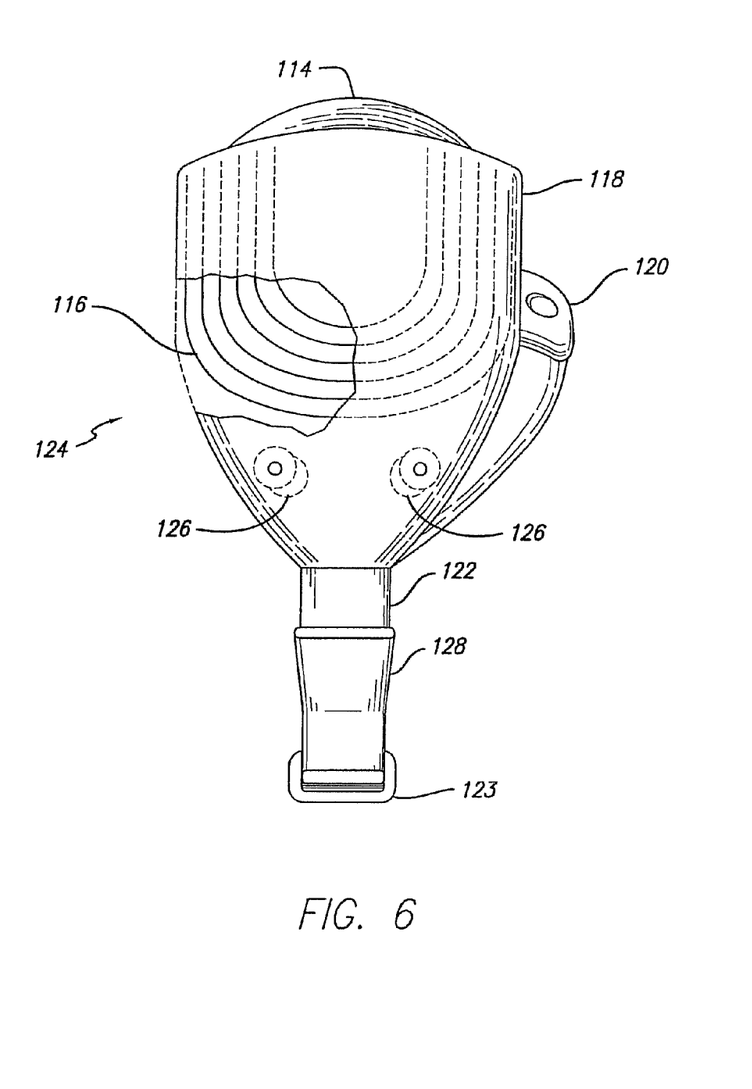
FIG. 6 is a side view of the implanted portion of the preferred visual prosthesis showing the fan tail in more detail.

FIG. 6 shows a side view of the implanted portion of the retinal prosthesis, in particular, emphasizing the fan tail 124. When implanting the retinal prosthesis, it is necessary to pass the strap 122 under the eye muscles to surround the sclera. The secondary inductive coil 116 and molded body 118 must also follow the strap under the lateral rectus muscle on the side of the sclera. The implanted portion of the retinal prosthesis is very delicate. It is easy to tear the molded body 118 or break wires in the secondary inductive coil 116. In order to allow the molded body 18 to slide smoothly under the lateral rectus muscle, the molded body is shaped in the form of a fan tail 24 on the end opposite the electronics package 114.

Accordingly, what has been shown is an improved method of making a neural prosthesis and improved method of stimulating neural tissue. While the invention has been described by means of specific embodiments and applications thereof, it is understood that numerous modifications and variations could be made thereto by those skilled in the art without departing from the spirit and scope of the invention. In particular, the preferred embodiment describes a retinal prosthesis for artificial vision. It should be obvious to one skilled in the art that the invention has broad applicability to other types of neural stimulation. It is therefore to be understood that within the scope of the claims, the invention may be practiced otherwise than as specifically described herein.

The invention claimed is:

1. A visual prosthesis comprising:
a video input device, providing video data;
a video processing unit collecting said video data from said video input device, the video processing unit including means for downloading, storing and changing, situation dependent filter information from a detachable remote computer including a storage device, said video processing unit further including means for processing said video data according to said filter information, said means for storing including non-volatile memory to preserve filter data when power is lost; and
an array of electrodes stimulating visual neural tissue according to said video data processed according to said filter information.

2. The visual prosthesis according to claim 1, further comprising safety checks which prevent said filter information from generating harmful signals.

3. The visual prosthesis according to claim 1, wherein said filter information comprises algorithms and parameters.

4. The visual prosthesis according to claim 1, wherein said video input device is a higher resolution than said electrode array.

5. The visual prosthesis according to claim 1, wherein said filter information is a reverse image filter.

6. The visual prosthesis according to claim 1, wherein said filter information is a contrast increasing filter.

7. The visual prosthesis according to claim 1, wherein said filter information is an edge detection filter.

8. The visual prosthesis according to claim 1, wherein said filter information is a movement detection filter.

9. The visual prosthesis according to claim 1, wherein said means for downloading includes means for error checking.

10. The visual prosthesis according to claim 1, wherein said means for down loading includes means for authenticity checking.

11. A visual prosthesis system comprising:
a detachable computer for storing a plurality of alternative sets of situation dependent video filter information;
a video input device, providing video data;
a video processing unit including:
means for receiving at least one of said alternative sets of video filter information from said detachable computer, said video filter information comprising video filter executable code and video filter data,
means for storing at least one of said alternative sets of video filter information, said video filter executable code and said video filter data, said means for storing including non-volatile memory to preserve filter data when power is lost, means for replacing said at least one of said alternative sets with another of said alternative sets, means for receiving said video data from said video input device, and means for processing said video data according to said at least one of said alternative sets of video filter information; and an array of electrodes stimulating visual neural tissue according to said video data processed according to said at least one set of alternative video filter information.

12. The visual prosthesis according to claim 11, wherein the downloading of said situation dependent filter information is to a non-volatile memory.

13. The visual prosthesis according to claim 11, wherein the processing of said video data generates a pixelized image.

14. The visual prosthesis according to claim 11, wherein the changing of said situation dependent filter information is a dynamic changing.

15. The visual prosthesis according to claim 11, wherein the downloading of situation dependent filter information uses a peer to peer communication protocol.

* * * * *